United States Patent [19]

Yim et al.

[11] Patent Number: 4,871,538
[45] Date of Patent: Oct. 3, 1989

[54] INSOLUBLE COPPER-ALPHA INTERFERON COMPLEX

[75] Inventors: Zachary Yim, Paramus; Martin Zupon, Basking Ridge; Imtiaz Chaudry, Denville, all of N.J.

[73] Assignee: Schering Corporation, Kenilworth, N.J.

[21] Appl. No.: 72,487

[22] Filed: Jul. 13, 1987

[51] Int. Cl.[4] .................... A61K 45/02; C07K 15/26
[52] U.S. Cl. .................................. 424/85.7; 530/351
[58] Field of Search ................. 424/85, 85.7; 530/351

[56] References Cited

U.S. PATENT DOCUMENTS 4,289,690  9/1981  Pestka et al. ..................... 424/85
4,496,537  1/1985  Kwan ................................ 424/85

FOREIGN PATENT DOCUMENTS 51783  6/1982  European Pat. Off. .
32134  8/1984  European Pat. Off. .

OTHER PUBLICATIONS

Ruberstein, *Biochem. Biophys. Acta.*, 695 (1982), pp. 5–16.
Nagata et al., *Nature*, 284 (1980), pp. 316–320.

*Primary Examiner*—Blondel Hazel
*Attorney, Agent, or Firm*—Anita W. Magatti; James R. Nelson; Stephen I. Miller

[57] ABSTRACT

An insoluble copper-alpha interferon complex useful for injectable pharmaceutical compositions is disclosed.

10 Claims, No Drawings

INSOLUBLE COPPER-ALPHA INTERFERON COMPLEX

SUMMARY OF THE INVENTION

The present invention relates to an insoluble copper-alpha interferon complex useful as an injectable dosage from for administering alpha interferon.

BACKGROUND

Injectable pharmaceutical formulations are well known in the art. Usually such formulations are in the form of dispersions such as colloids, emulsions and suspensions. More recently, sustained release injectable formulations comprising polymers have been used.

Interferons are a family of proteins which exhibit antiviral activity against certain viruses and anticancer activity against certain cancers. Interferons include natural or recombinant alpha (leucocyte), beta (fibroblast) and gamma (immune) interferon, but alpha interferons are preferred for use in the compositions of this invention. Human alpha interferon is a naturally occurring mixture of at least eleven components including those designated $alpha_1$ and $alpha_2$ interferon, the latter being more preferred in this invention. Human alpha interferon exhibiting biological properties similar to naturally occurring alpha interferon can be made by recombination methods. Rubenstein, *Biochem. Biophys. Acta.*, 695, 5-16 (1982); Nagata et al., *Nature*, 284, 316–320 (1980); EP 32,134; and U.S. Patent 4,289,690 disclose methods for preparing $alpha_2$ interferon. Also included within the scope of this invention are the so-called alpha hybrid interferons wherein fragments of two or more native alpha interferon species are joined (See, for example, EP 51,783). Parenteral administration of $alpha_2$ interferon has been reported to be effective in the treatment of Kaposi's sarcoma, basal cell carcinoma, multiple myeloma and viral warts. The effective dose of alpha interferon can be easily determined by those skilled in the art.

DETAILED DESCRIPTION

The present invention relates to an insoluble complex comprising copper and alpha interferon. The complex comprises 0.01 to 1 mg alpha interferon per ml of a compatible buffer adjusted to pH 7.5 to 8.2 and 0.05 to 0.09 mg/ml of cupric ions. The cupric ions are provided by a copper salt selected from copper acetate, copper chloride, copper citrate and copper sulfate, with copper acetate being preferred. A pH of 7.8 is preferred for the complex.

While simple in terms of the number of components present, this invention represents a complex and unpredictable equilibrium phenomenon between alpha interferon and copper. For maximum complex formation, the optimal concentrations of alpha interferon and copper and the optimal pH range of the complex fall within narrow limits. A 20% variation in concentration of copper in either direction (i.e., higher or lower concentration) results in a 50% drop in the amount of insoluble complex formed.

A preferred method of preparing the complex is to adjust a buffered alpha interferon solution to pH 7.5 to 8.2, preferably 7.8, with a base, preferably sodium hydroxide, then to add an appropriate aliquot of an aqueous 0.01 to 0.1 N copper salt solution. Any appropriate alpha interferon solution may be used, e.g., bulk solutions (i.e., previously unlyophilized) or reconstituted alpha interferon solutions, but the alpha interferon solution must not contain human serum albumin (HSA) since very small amounts of HSA solubilize the complex. For example, a complex containing 1 mg alpha interferon is totally solubilized by 0.1 mg HSA.

Injectable pharmaceutical compositions using the alpha interferon-copper complex of this invention are sustained release in that the alpha interferon must be released from the complex before it enters the system of the patient, but due to the solubility of the complex in the presence of HSA and the high concentrations of HSA in the blood, duration of alpha interferon administration is not necessarily the major advantage of this invention. The instant compositions, however, are stable on storage and can be advantageously used to provide moderately controlled release of interferon in a localized area of the body. If a certain soluble fraction is desired for immediate release, the ratio of components can be changed or the pH may be adjusted.

Alpha interferon compositions of this invention comprise 0.2 to $20 \times 10^6$ International Units of alpha interferon per dose, with a typical dosage volume being 0.1 ml.

Any chemically and pharmaceutically compatible buffer may be used to prepare the interferon solution, with phosphate buffer being preferred. Interferon solutions show maximum stability of pH 6.5 to 8.0, preferably 7.0 to 7.4 (See U.S. Pat. No. 4,496,537). Sodium hydroxide is preferred for adjusting the pH of the interferon solution of pH 7.5 to 8.2 prior to formation of the complex. The buffering agent must not have a strong affinity for copper, as this would tend to remove copper from the complex.

Release of alpha interferon from the complex is not measurable in vitro since it is not solubilized by dilution, but rather by displacement of physiological chelators as well as serum albumin. The in vivo release rate can be measured by using radio-iodinated alpha interferon and monitoring the disappearance of radioactivity at the injection site and the presence of radioactivity in serum and urine.

Formation of the complex was measured by scattering at 700 nm and by measurement of the soluble protein remaining in the supernatant by high pressure liquid chromatography.

Following is an example of the preparation of an alpha interferon-copper complex of the invention.

EXAMPLE 1

| Ingredients | mg/ml |
| --- | --- |
| Lyophilized Alpha Interferon | 1.0 ($200 \times 10^6$ I.U.) |
| Copper Acetate | 0.2 |
| Sodium Phosphate, Dibasic | 2.27 |
| Sodium Phosphate, Monobasic | 0.55 |
| Sodium Hydroxide | 0.6 |
| Water for injection | 1.0 ml |

Dissolve the monobasic and dibasic sodium phosphates in a portion of the water for injection. Dissolve the lyophilized interferon in this solution and adjust to pH 7.8 with the sodium hydroxide. Add the copper acetate and agitate. Bring the solution to final volume with the remaining water for injection. Preferably, th sodium hydroxide and copper acetate are added as concentrated aqueous solutions (e.g. for copper acetate, 100 microliters of a 2 mg/ml aqueous solution).

We claim:

1. A pharmaceutical composition comprising a parenterally acceptable insoluble cupric ion-alpha interferon complex wherein the alpha interferon is present at 0.01 to 1 mg/ml complex.

2. A composition of claim 1 comprising 0.01 to 1 mg alpha interferon and 0.05 to 0.09 mg cupric ions per ml of compatible buffer at pH 7.5 to 8.2, wherein the cupric ions are provided by a copper salt selected from the group consisting of copper acetate, copper chloride, copper citrate and copper sulfate.

3. A composition of claim 2 suitable for injection.

4. A composition of claim 2 comprising copper acetate.

5. A composition of claim 2 wherein the buffer is pH 7.8.

6. A composition of claim 2 comprising 1 mg alpha interferon per ml.

7. A composition of claim 4 comprising 0.2 mg copper acetate/ml.

8. A composition of claim 2 wherein the buffer is phosphate buffer.

9. A composition of claim 2 comprising 1 mg alpha interferon and 0.2 mg copper acetate per ml of a phosphate buffer at pH 7.8.

10. A composition of claim 9 comprising 2 to $200 \times 10^6$ International Units of alpha interferon per ml.

* * * * *

UNITED STATES PATENT AND TRADEMARK OFFICE
CERTIFICATE OF CORRECTION

PATENT NO. : 4,871,538
DATED : Oct. 3, 1989
INVENTOR(S) : Zachary Yim et al.

It is certified that error appears in the above-identified patent and that said Letters Patent is hereby corrected as shown below:

On the title page, line 1 of the list of inventors, change "Martin" to -- Michael --.

Signed and Sealed this

Ninth Day of October, 1990

Attest:

HARRY F. MANBECK, JR.

*Attesting Officer*   *Commissioner of Patents and Trademarks*